US008185209B2

(12) United States Patent
Dantus

(10) Patent No.: US 8,185,209 B2
(45) Date of Patent: May 22, 2012

(54) METHODS TO EXTEND VISION TO INFRARED WAVELENGTHS

(75) Inventor: Marcos Dantus, Okemos, MI (US)

(73) Assignee: Board of Trustees Operating Michigan State University, East Lansing, MI (US)

( * ) Notice: Subject to any disclaimer, the term of this patent is extended or adjusted under 35 U.S.C. 154(b) by 2329 days.

(21) Appl. No.: 10/749,095

(22) Filed: Dec. 17, 2003

(65) Prior Publication Data

US 2011/0171320 A1      Jul. 14, 2011

Related U.S. Application Data

(60) Provisional application No. 60/438,043, filed on Jan. 3, 2003.

(51) Int. Cl.
*A61N 1/00*      (2006.01)
(52) U.S. Cl. .................. 607/54; 424/617; 424/130.1
(58) Field of Classification Search .............. 607/54; 424/617, 130.1
See application file for complete search history.

(56) References Cited

U.S. PATENT DOCUMENTS

| | | | | |
|---|---|---|---|---|
| 4,857,228 | A * | 8/1989 | Kabay et al. | 252/301.4 S |
| 5,024,223 | A * | 6/1991 | Chow | 607/53 |
| 5,554,187 | A | 9/1996 | Rizzo, III | |
| 5,824,072 | A * | 10/1998 | Wong | 128/898 |
| 5,990,095 | A * | 11/1999 | Falk et al. | 514/54 |
| 6,298,270 | B1 * | 10/2001 | Nisch et al. | 607/54 |
| 6,319,240 | B1 | 11/2001 | Beck | |
| 6,331,313 | B1 | 12/2001 | Wong et al. | |
| 6,389,317 | B1 * | 5/2002 | Chow et al. | 607/54 |
| 6,685,986 | B2 * | 2/2004 | Oldenburg et al. | 427/214 |
| 6,755,530 | B1 * | 6/2004 | Loftus et al. | 351/246 |
| 7,008,559 | B2 * | 3/2006 | Chen | 252/301.5 S |
| 2002/0141760 | A1 * | 10/2002 | Resnick | 396/661 |
| 2005/0239048 | A1 * | 10/2005 | Lawandy | 435/4 |
| 2008/0269119 | A1 * | 10/2008 | Griffith et al. | 514/12 |

OTHER PUBLICATIONS

"Retinal Diseases", John G. Flannery, Ph.D., Optometry 10—The Eye and Vision in a Changing Environment, Lecture Apr. 1, 1999, Instructor: A. J. Adams, Website: http://spectacle.berkeley.edu/class/opt10/lec9.shtml, May 14, 2002.
"Scientists Send in the Small Guns to Help Blow Away Brain Cancer", Rosemary Clandos, Small Times: News about MEMS, Nanotechnology and Microsystems, Website: http://www.smalltimes.com/document_display.cfm?document_id=229, pp. 1-3, Mar. 19, 2002.
Abstract—"Co-delivery of an antisense oligonucleotide and 5-fluorouracil using sustained release poly (lactide-co-glyclide) microsphere formulations for potential combination therapy in cancer", Hussain M et al., International Joouornal of Pharmaceutics, 234 (1-2): 129-138 Mar. 2, 2002, ISI Web of Science Website: http://wos.isiglobalanet2.com/CIW.cgi, p. 1, Mar. 19, 2002.
Abstract—"Inhibition if HIV-1 in cell culture by oligonucleotide-loaded nanoparticles", Berton M, et al., Pharmaceutical Research, 18(8): 1096-1101, Aug. 2001, ISI Web of Science Website: http://wos.isiglobalnet2.com/CIW.cgi, p. 1, Mar. 19, 2002.
Abstract—"Ligand coated nanosphere adhesion to E- and P-selectin under static and flow conditions", Blackwell JK, et al., Annals of Biomedical Engineering, 29(6): 523-533, Jun. 2001, ISI Web of Science Website: http://wos.isiglobalnet2.com/CIW.cgi, p. 1, Mar. 19, 2002.
Abstract—"Design of folic acid-conjugated nanoparticles for drug targeting", Stella B, et al., Journal of Pharmaceutical Sciences, 89(11): 1452-1464, Nov. 2000, ISI Web of Science Website: http://wos.isiglobalnet2.com/CIW.cgi, p. 1, Mar. 19, 2002.
Abstract—"Development of a cancer vaccine: peptides, proteins, and DNA", Shiku H, et al., Cancer Chemotherapy and Pharmacology, 46: S77-S82 Suppl. S, Jun. 2000, ISI Web of Science Website: http://wos.isiglobalnet2.com/CIW.cgi, p. 1, Mar. 19, 2002.
Abstract—"Hyperthermia enables tumor-specific nanoparticles delivery: Effect of particle size", Kong G, et al., Cancer Research, 60(16): 4440-4445, Aug. 15, 2000, ISI Web of Science Website: http://wos.isiglobalnet2.com/CIW.cgi, p. 1, Mar. 19, 2002.
Abstract—"Antisense Oligonucleotides Absorbed to Polyalkylcyanoacrylate Nanoparticles Specifically Inhibit Mutated HA-RAS-Medicated Cell-Proliferation and Tumorigenicity in Nude-Mice", Schwab G, et al., Proceedings of the National Academy of Sciences of the United States of America, 91(22): 10460-10454, Oct. 25, 1994, ISI Web of Science Website: http://wos.isiglobalnet2.com/CIW.cgi, p. 1, Mar. 19, 2002.
Abstract—Subcutaneous and intravenous delivery of diagnostic agents to the lymphatic system: applications in lymphoscintigraphy and indirect lymphography, Moghimi SM, et al., Advanced Drug Delivery Reviews, 37(1-3): 295-312 May 4, 1999, ISI Web of Science Website: http://wos.isiglobalnet2.com/CIW.cgi, p. 1., Mar. 19, 2002.
Abstract—"Plasmid DNA absorbed onto cationic microparticles mediates target gene expression and antigen presentation by dendritic cells", Denis-Mize KS, et al., Gene Therapy, 7(24): 2105-2112, Dec. 2000, ISI Web of Science Website: http://wos.isiglobalnet2.com/CIW.cgi, p. 1, Mar. 19, 2002.
Abstract—"New light emission processes in inorganic materials", Gerner P, et al., Chimia, 55(12): 1021-1024, 2001, ISI Web of Science Website: http://wos.isiglobalnet2.com/CIW.cgi, p. 1, Mar. 19, 2002.
Abstract—Up-conversion luminescence of Mn2+ in ZnS: Mn2+ nanoparticles, Ceh W, et al., Physical Review B, 64(4): art. No. 041202 Jul. 15, 2001, ISI Web of Science Website: http://wos.isiglobalnet2.com/CIW.cgi, p. 1, Mar. 19, 2002.
Abstract—"Synthesis and photoluminesence of nanocrystalline ZnS: Mn2+", Suyver JF, et al., Nano Letters, 1(8): 429-433, Aug. 2001, ISI Web of Science: http://wos.isiglobalnet2.com/CIW.cgi, p. 1, Mar. 19, 2002.

(Continued)

*Primary Examiner* — Mark Hellner
(74) *Attorney, Agent, or Firm* — Harness, Dickey & Pierce, P.L.C.

(57) ABSTRACT

In a method for visualizing an object under conditions of low ambient light, the object to be visualized is exposed to incident electromagnetic radiation having a wavelength greater than what can normally be seen by the naked eye. Light reflected from the object is then perceived with an enhanced eye. The enhanced eye contains an up-conversion material optically coupled to the photoreceptors. Up-conversion materials absorb in the infrared and luminesce in the visible. Particles containing such materials are delivered to the eye where they are optically coupled to the retina or photoreceptor cells and nearby tissues. There they provide in-situ up-conversion of infrared frequencies (from about 700 to about 11,000 nm) to the otherwise unaided eye.

85 Claims, No Drawings

OTHER PUBLICATIONS

Abstract—"The effect of particle morphology and crystallite size on the upconversion luminesence properties of erbium and ytterbium co-doped yttrium oxide phosphors", Silber J, et al., Journal of Physical Chemistry B, 105(5): 948-953, Feb. 8, 2001, ISI Web of Science Website: http://wos.isiglobalnet2.com/CIW.cgi, p. 1, Mar. 19, 2002.

Abstract—"Infrared-to-visible upconversion in Nd3+-doped chalcolhalide glasses", Balda R, et al., Physical Review B, (64(14): art.No. 144101, Oct. 1, 2001, ISI Web of Science; http://wos.igiglobalnet2.com/CIW.cgi, p. 1, Mar. 19, 2002.

"Twentyfold blue upconversion emission enhancement through thermal effects in $Pr^{3+}/Yb^{3+}$-codoped fluoroindate glasses excited at 1.064 μm", A.S. Oliveira, et al., Journal of Applied Physics, vol. 87, No. 9, pp. 4274-4278, May 1, 2000.

"The pump power dependence of the femtosecond relaxation of CdSe nanoparticles observed in the spectral range from visible to infrared", Clemens Burda, et al. Journal of Chemical Physics, vol. 116, No. 9, pp. 3828-3833, Mar. 1, 2002.

"Efficient infrared imaging upconversion via quantum coherence", Robert W. Boyd, et al., Applied Physics Letters, vol. 77, No. 22, pp. 3559-3561, Nov. 27, 2000.

Website Article—Eyegate Patented Disposable System, Website: www.optisgroup.com, p. 6, May 15, 2002.

Website Article—Zenon Labeling Technology, Website: www.probes.com, pp. 2-6, Revised Mar. 7, 2001.

Section 16.1—"Probes for Following Receptor Binding, Endocytosis and Exocytosis", pp. 1-16, Updated: Oct. 6, 2002, Website: www.probes.com/handbook/sections/1601.html, Oct. 22, 2002.

Molecular Probes, Photo g000457, "A transverse section of fixed zebrafish regina probed with FRet43", p. 1, Website: www.probes.com/servlets/photo?fileid=g000457, Oct. 22, 2002.

"Nanosphere-antibody conjugates with releasable fluorescent probes", R.N. Thomas, et al., Frensius J Anal Chem (2001) 369: 477-482, pp. 6, Springer-Verlag 2001.

Research Paper, Synthesis, simulation & spectroscopy: physical chemistry of nanocrystals, J.F. Suyer, Debye Institute, Physics and Chemistry of Condensed Matter, Utrecht University, pp. 32, Undated.

"Nanotechnology in BioMedical Applications", Bruce A. Holm, et al., School of Medicine and Biomedical Sciences and the Institute for Lasers, Photonics and Biophotonics University at Buffalo State University of NewYork, Mol. Cryst. Liq. Cryst., vol. 374, pp. 589-598., Taylor & Francis, 2002.

"980 nm excited upconversion in an Er-doped ZnO-TeO2 glass", Fiorenzo Vetrone, et al., Applied Physics Letters, vol. 80, No. 10, p. 1752-1754. Mar. 11, 2002.

"Enhancement of Red Emission ($^4F_{frax;9;2}$-$^4I_{frax;15;2}$) via Upconversion in Bulk and Nanocrystalline Cubic $Y_2O_3$:$Er^{3+}$", John A. Capobianco, et al., J. Phys. Chem. B 2002, 106, pp. 1181-1187, 2002 American Chemical Society, Jan. 18, 2002.

"Upconversion in $Er^{3+}$:$ZrO_2$ Nanocrystals", Amitava Patra, et al., Institute for Lasers, Photonics and Biophotonics, University at Buffalo, The State University of New York, J. Phys. Chem. B 2002, pp. 1909-1912, Feb. 2, 2002.

Abstract—"Low amplification and fast visual pigment phosphorylation as mechanisms characterizing cone photoresponses", Tachibanaki S, et al., Proceedings of the National Academy of Sciences of the United States of America 98(24): 14044-14049 Nov. 20, 2001, ISI Web of Sciences Website: http://isi6:webofscience.com/CIW.cgi, p. 1, May 7, 2002.

Abstract—"Signal amplification: Let's turn down the lights", Lagnado L, Current Biology 12(6): R215-R217 Mar. 19, 2002, ISI Web of Science Website: http://isi6.webofscience.com/CIW.cgi, p. 1, May 7, 2002.

Abstract—"Neural image enhancement allows honeybees to see at night", Warrant E, et al., Proceedings of the Royal Society of London Series B-Biological Sciences, 263(1376): 1521-1526 Nov. 22, 1996, p. 1, ISI Web of Science Website: http:isi6.webofscience.com/CIW/cgi, May 7, 2002.

"Our Research, Drug Delivery: Trojan Horses", Gerald J. Chader, The Foundation Fighting Blindness, Science and Research, Website: http://www.blindness.org/html/science/wroverview.n, p. 4, May 12, 2002.

"Pharmaceutical and Biotechnology Update", Dr. Tim Schoen, Science and Research pp. 3, Website: http://www.blindness.org/html/science/wdelivery.n, May 12, 2002.

"Photopic Luminous Efficiency Function of the Human Retina", p. 5, Website: http://4colorvision.com/files/photopiceffic, May 14, 2002.

"Human Cone Action Spectra", Cone Action Spectra, Website: http://www.unm.edu/toolson/human_cone_response, pp. 1-2, May 14, 2002.

"Color Vision", Peter Gouras, Webvision: Color Vision, pp. 26, Website: http://webvision.med.utah.edu/color, May 14, 2002.

Sensitivity Regulation (Light and Dark Adaptation), Mark E. McCourt, Revised: Sep. 22, 2001, p. 4, Website: http://www.psychology.psyn.ndsu.nodake.e...regulations/sensitivity%20regulation. May 14, 2002.

"The Purkinje Shift", Website: http://www.cquest.utoronto.ca/psych/psych280f/ch3/purkinje/ps.h., pp. 2, May 14, 2002.

"Recombinant Adenovirus and Ocular Gene Therapy", Jean Bennett, et al., p. 17, Released Jun. 2, 1999, Website: http:///222.rwetina-international.org/sc-news/topbenne.htm, May 14, 2002.

"Gene Therapy for Diseases of the Central Nervous System", CNS Diseases, p. 3, Website: http://www.medicine,uiowa.edu/davidsonlab/dns.htm, May 14, 2002.

"Pharmaceutical and Gene Therapy for Reginal Degenerations", Matthew M. LaVail, PhD, Professor of Anatomy and Opthalmology, p. 3, Website: http://www.ucsfeye.net/LaVailM.html, May 14, 2002.

"Naked Cell", Neuroteck SA, pp. 4, Website: http://www.neurotec.fr/technos/cellules-d.htm, May 14, 2002.

"Efficient photoreceptor-targeted gene expression in vivo by recombinant adeno-associated virus", John G. Flannery, et al., Proc. Natl. Acad. Sci., vol. 94, pp. 6916-6921, Jun. 1997.

"Stable transgene expression in rod photoreceptors after recombinant adeno-associated virus mediated gene transfer to monkey retina", Jean Bennett, et al., Proc. Natl. Acad. Sci. Wol. 96, pp. 9920-9925, Aug. 1999.

"Gene regulation, development and functional organization of the vertebrate retina", Vijay P. Sarthy, PhD., Website: http://www.nums.nwu.edu/igp/facindex/SarthyV.html, pp. 2, May 14, 2002.

"Survival Factors As Potential Therapeutic Agents for Retinal Degenerations: Status and Prospects", Matthew M. LaVail, et al., Beckman Vision Center, Website: http://djo.harvard.edu/meei/OA/lav/INDEX.html, pp. 5, May 14, 2002.

Abstract—"Ocular disposition and tolerance of ganciclovir-loaded albumin nanoparticles after intravitreal injection in rats", Merodio M., et al., Biomaterials, 23(7): 1587-1894 Apr. 2002, ISI Web of Science, pp. 1, May 7, 2002.

Abstract—"Suppression of Fas-medisted hepatic apoptosis by caspase inhibitors-encapsulated nanoparticles bearing poly-(N-p-vinylbenzyl-O-beta-D-galactopyranosyl-[1-4]-D-glucoonamide", Sibuya I, et al., Biotechnology Letters, 22(23): 1855-1859 Dec. 2000, ISI Web of Science, p. 1, May 7, 2002.

Abstract—"Supersensitive time-resolved immunofluorometric assay of free prostate-specific antigen with nanoparticle label technology", Soukka T, et al., Clinical Chemistry, 47(7): 1269-1278 Jul. 2001, ISI Web of Science, pp. 1, May 7, 2002.

Abstract—"Solid substrate phosphorescent immunoassay based on bioconjugated nanoparticles", Sun BQ, et al., Analytical Letters 34(10): 1627-1637 (2001), ISI Web of Science, p. 1, May 7, 2002.

Abstract—"Conjugation of biomolecules with luminophore-doped silica nanoparticles for photostable biomarkers", Santra S., et al., Analytical Chemistry, 73(20): 4988-4993 Oct. 15, 2001, ISI Web of Science, p. 1, May 7, 2002.

Abstract—"Design of biodegradable particles for protein delivery", Vila A., et al., Journal of Controlled Release, 78(1-3: 15-24 Jan. 17, 2002, ISI Web of Science, 1 pg, May 7, 2002.

Abstract—Opthalmic drug delivery systems—Recent advances, Le Bourlais C, Progress in Retinal and Eye Research, 17(1): 33-58 Jan. 1998, ISI Web of Sciences, May 7, 2002.

Abstract—"Preparation of aminodextran-CdS nanoparticles complexes and biologically active antibody-aminodextran-CdS nanoparticles conjugates", Soldi I, et al., Langmuir, 16(7)3: 3107-3118 Apr. 4, 2000, ISI Web of Science, May 7, 2002.

Abstract—"Morphological and functional damage of the retina caused by intravitreous indocyanine green in rat eyes", Enaida H, et al., Graefes Archive for Clinical and Experimental Opthalmology, 240(3): 209-213 Mar. 2002, ISI Web of Science, p. 1, May 7, 2002.

Abstract—"Choriocapillaris photodynamic therapy using indocyanine green", Costa RA, et al., American Journal of Ophthalmology, 132(4): 557-565 Oct 2001., ISI Web of Science, p. 1, May 15, 2002.

Abstract—"Dynamci observation of selective accumulation of photosensitizer and its photodynamic effects in rat experimental choroidal neovascularization", Hikichi T, et al., Retina-The Journal of Retinal and Vitreous Diseases, (21)2: 126-131 2001, ISI Web of Science, p. 1., May 15, 2002.

Abstract—"Selective photodynamic effects of the new photosensitizer ATX-S10(Na) on choroidal neovascularization in monkeys", Obana A, et al., Archives of Ophthamology, 118(5): 650-658 May 2000., ISI Web of Science, p. 1., May 15, 2002.

Abstract—"Identification of novel molecular components of the photreceptor connecting cilium by immunoscreens", Schmitt A., et al., Experimental Eye Research, 73(6):837-849 Dec. 2001, ISI Web of Science, p. 1., May 15, 2002.

Abstract—"Transscleral Coulomb-controlled iontophosoesis of methyl prednisolone into the rabbit eye: Influence of duration of treatment, current intensity and drug concentration on ocular tissue and fluid levels", Behar-Cohen FF, et al., Experimental Eye Research, 74(1): 51-59 Jan. 2002, ISI Web of Science, p. 1., May 15, 2002.

Abstract—"Induction of gene into the rabbit eye by iontophoresis: Preliminary report", Asahara T, et al., Japanese Journal of Ophthalmology, 45(1): 31-39 Jan.-Feb. 2001., ISI Web of Science, p. 1., May 15, 2002.

Abstract—"Biodegradable scleral implant for controlled intraocular delivery of betamethasone phosphate", Kunou N, et al., Journal of Medical Materials Research, 51(4): 635-641 Sep. 2000, ISI Web of Science, p. 1., May 15, 2002.

Abstract—"Determination of ocular toxicity in multiple applications of foscarnet iontophoresis", Yoshizumi MO, et al., Journal of Ocular Pharmacology and Therapeutics, 13(6): 529-536 Dec. 1997, ISI WEb of Science, p. 1., May 15, 2002.

\* cited by examiner

METHODS TO EXTEND VISION TO INFRARED WAVELENGTHS

CROSS REFERENCE TO RELATED APPLICATIONS

This application claims priority to U.S. Provisional Application Ser. No. 60/438,043, filed Jan. 3, 2003, which is incorporated by reference herein.

FIELD OF THE INVENTION

The present invention relates to optical materials and methods for delivering them to the eye. It further relates to methods for enhancing vision under conditions of low illumination.

BACKGROUND OF THE INVENTION

The spectrum of solar irradiance can be described as black body radiation with a characteristic temperature of 5800 K. Taking into account the transmission window of visibility of the eye, which cuts off near 350 nm and extends to the infrared and the absorption of atmospheric gases, light available naturally for vision extends from 400 nm to about 1300 nm. Of the available light, the eye generally uses a relatively narrow spectral range for vision. For example, scotopic vision provided for rod cells is centered at about 505 nm and ranges from 435-600 nm. The rods allow for vision under low-light conditions. On the other hand, cones are responsible for color vision and provide vision under conditions of high luminosity. Photopic vision provided by the cones is centered near 550 nm and extends from about 450 to 650 nm. The wavelength region above that in the visible range detected by the rods and cones is known as the infrared.

There is a demand for methods that allow humans and other animals to see in the infrared region of the spectrum, under low light conditions, and/or at wavelengths that cannot be observed by unaided eyes. At present, for example, the military equips soldiers with devices to allow them night vision capabilities. The devices are expensive, often costing $1,000 or more per soldier. Assault aircrafts, helicopters, tanks, and other vehicles are equipped with yet more expensive versions of infrared viewing equipment.

A conventional infrared viewer and night vision scope contains imaging optics, a phosphor screen containing materials that through absorption of infrared photons convert that energy into the visible, an image intensifier that amplifies the un-converted light, and additional optics to render a clear picture for the user. The units are generally heavy, cumbersome, expensive, and fragile, have a very narrow field of view, have no active focusing or light intensity regulation, and require batteries or other power supplies.

The process of up-conversion refers to the conversion of one or more photons of longer wavelengths (less energy) to one or more photons of a shorter wavelength (more energy). Typically, the process proceeds by a two-photon absorption followed by one-photon emission. For example, 2 photons of 800 nm light may be absorbed followed by emission of a visible photon with a wavelength of 400 nm. The probability of two-photon absorption depends on a number of parameters; most importantly of which is a resonance at either the one or two photon levels. When there is no resonance at the one-photon level, it is necessary for two photons to coincide at the up-conversion particle. This typically requires high intensity light, for example light from pulsed laser sources or illumination from non-classical light resulting from two photon down conversion.

Up-conversion can be made much more efficient when there is a one photon resonance that is long lived. In these cases, the light intensity required for two-photon absorption is greatly reduced. In the presence of a one photon resonance, the timing between photons arriving at the up-conversion particles should equal the lifetime of the intermediate state, which can be as long as a microsecond.

Recently, a number of up-conversion materials, also called phosphors, have been produced. A typical up-conversion material involves a sensitizer (a compound that has an intermediate electronic state in near resonance with the wavelength that needs to be up-converted) and an emitter (a compound that accepts the energy from the sensitizer and emits visible light). Sensitizers may involve single or combinations of lanthanoid ions such as $Yb^{3+}$, which has a resonance near 1000 nm. Additionally, semiconductor materials such as Si, GaAs, GaN, Ge, InN, and ZnS, having band gaps in the infrared may be used.

Targeting of nanoparticles and other sensor molecules such as dyes or therapeutic compounds to specific cells is an active area of research. It has been demonstrated how to target specific cells, for example, for cancer treatments. Such methods include antibody targeting, aptamers, and recombinant viruses.

For delivery to the eye, eye drops are generally ineffective because there is a barrier that prevents penetration of foreign substances from the outer layers of the eye to the interior. Other methods, such as ocular injection or implantation, are less desirable because of fear, discomfort, inflammation, and other side effects in the patient.

It would be desirable to provide methods for enhancing night vision that overcome the limitations of existing night vision equipment. It would also be desirable to provide up-conversion materials and methods for their delivery directly to the eye.

SUMMARY OF THE INVENTION

In one aspect, the methods of the invention utilize up-conversion materials that absorb in the infrared and luminesce in the visible. Particles containing such materials are delivered to the eye where they are optically coupled to the retina or photoreceptor cells and nearby tissues. There they provide in-situ up-conversion of infrared frequencies (from about 650 to 1500 nm, preferable about 800 to about 1300 nm) to the otherwise unaided eye.

In one embodiment, a method is provided for enhancing vision in an animal under conditions of low intensity light. The method comprises delivering up-conversion material to the eye of the animal. The up-conversion materials absorb infrared light at a wavelength above about 650 nm, and the materials luminesce in the visible range of the electromagnetic spectrum.

In another embodiment, a composition is provided that comprises a nanoparticle covalently bound to an antibody. The nanoparticle comprises up-conversion materials that absorb electromagnetic radiation having a wavelength greater than about 650 nm and luminesce in the visible region of the electromagnetic spectrum. The antibody is an antibody specific to a biomaterial component of the eye such as an eye protein.

In a further embodiment, the invention provides an animal, either human or non-human, having enhanced vision. An up-conversion material is optically coupled to the photoreceptors of the eye of the animal. In a preferred embodiment, the up-conversion material contains nanoparticles comprising the up-conversion materials, the nanoparticles being covalently bound to an antibody of an eye protein component.

In yet another embodiment, a method is provided for visualizing an object under conditions of low ambient light. The object to be visualized is exposed to incident electromagnetic radiation having a wavelength greater than what can normally be seen by the naked eye. Radiation reflected from the object is then perceived with an enhanced eye. The enhanced eye contains an up-conversion material optically coupled to the photoreceptors, as described above with respect to other embodiments. As above, the up-conversion materials absorb light of the wavelength reflected from the object, and luminesce in the visible region of the electromagnetic spectrum.

In another aspect, wavelength shifting materials are delivered to the eye of an animal subject to enhance vision. Methods and compositions for carrying out this aspect of the invention are similar to those described above relating to the up-conversion materials. An optical material is coupled to the photoreceptors of the eye. The optical material has the property of absorbing light at a particular frequency, and luminescing at a redder, i.e. longer, wavelength. In a preferred embodiment, the wavelength shifting materials are provided in the form of nanoparticles, preferably covalently bound to an antibody of a biomaterial, especially a protein, of the eye. Phosphorescent materials provide for integration to allow enhanced vision under low natural illumination. Other materials provide a shift from a lower wavelength to a higher wavelength, permitting better visualization of the higher wavelength.

DETAILED DESCRIPTION OF EMBODIMENTS OF THE INVENTION

The following description of preferred embodiments is merely exemplary in nature and is in no way intended to limit the invention, its application, or uses.

To enhance vision under conditions of low illumination, or to expand vision to wavelength regions outside the visible, up-conversion materials are delivered to the eye of an animal and optically coupled to the structures of the eye responsible for vision. By optically coupled is meant that the materials are placed in proximity to the photoreceptors of the eye, so that light emitted by the optically coupled materials goes directly to the photoreceptors, producing an image. Importantly, optically coupled materials are located in the eye behind the lens, which focuses the incident radiation onto the photoreceptors and the optically coupled up-conversion materials. In one embodiment, the optically coupled up-conversion materials respond to incident infrared light focused through the lens, and emit photons in the visible region of the spectrum, enabling the animal to visualize the infrared radiation.

The invention may be practiced in human or non-human animals by delivering the up-conversion materials to the eye of the animal. Non-limiting examples of non-human animals include, dogs, dolphins, crows, and horses. In a preferred embodiment, the up-conversion materials are delivered to the eye of a species of animal known to be readily trainable, such as a dog. Such an animal may be trained to respond to up-converted light resulting from incident photons of a single wavelength or of multiple wavelengths. Uses include security tagging of targets and individuals, such as at an airport. An animal could be trained to locate or follow an individual who has been tagged or "painted" by an operator using an infrared device. An advantage would be that the individual would not be aware he is under surveillance.

Alternatively, animals may be provided with broad-spectrum vision, enabling them to operate, for example, at night under conditions of low natural illumination. Military troops with such vision would have an advantage over an enemy that either could not see in the dark, or else could see only by using conventional night vision equipment, which is bulky, heavy and awkward, and which is prone to defeat by bright flashes of light that can temporarily blind an operator or damage the equipment.

In addition, people working with fiber optics that use infrared light, for example of about 1.5 microns (1500 nm) could be provided with the ability to visualize light of that wavelength. Such ability would simplify their work in certain situations.

In one embodiment, the up-conversion materials contain rare earth ions that exhibit two photon, anti-stokes luminescence by frequency up-converting infrared to visible light. Other up-conversion materials include, without limitation, semiconductor materials having a band gap in the infrared, and certain transition metals doped into an organic or inorganic host lattice.

The up-conversion materials contain two functional elements, which may be supplied by one and the same chemical substance or may be supplied by two or more chemical substances. The sensitizer is a functional component of the up-conversion material that provides for absorption of light in the infrared. Preferably, absorption of a photon of infrared light by the sensitizer results in an excited state with a lifetime on the order of milliseconds. The second functional component of the up-conversion materials is an emitter, also called an acceptor. The emitter or acceptor is capable of transferring the energy from the excited state of the sensitizer. Thereafter, the acceptor is capable of absorbing a second photon. After absorbing the second photon, the emitter relaxes to the ground state by luminescing in the visible region of the electromagnetic spectrum. The net result is an up-conversion from incident light in the infrared region to visible light, generally in the wavelength range from about 400 to 700 nm, and more preferably from about 425 nm to 650 nm.

Up-conversion materials useful in the invention are generally well known, and find use for example as phosphors in night vision goggles and the like. As mentioned above, the sensitizers are generally selected from among the group consisting of lanthanide ions (also called lanthanoid ions) and semiconductor materials having a band gap in the infrared region. In addition, some up-conversion materials contain transition metals in special lattices as noted above.

Lanthanide ions capable of absorbing light in the infrared region and useful as sensitizers in the up-conversion materials of the invention include +3 ions of lanthanide elements such as cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), and lutetium (Lu). Semiconductor materials useful in the invention include, without limitation, silicon, gallium arsenide, zinc sulfide, cadmium selenide, and calcium sulfide.

Up-conversion materials are generally prepared by doping a carrier material with a small amount of the lanthanoid ion, semiconductor material, or transition metal. Non-limiting examples of specific phosphors capable of up-converting infrared to visible light include: yttrium oxide co-doped with $Er^{3+}$ and $Yb^{3+}$, prepared by precipitation in the presence of EDTA, described in J. Phys. Chem. B 105, 948-953 (2001); $Nd^{3+}$ doped chalcohalide glasses, described in Phys. Rev. B 64, art #144101, Oct. 1, 2001; $Yb^{3+}$ sensitized $Pr^{3+}$ doped fluorinate glasses, described in J. Appl. Physics 87, 4274-4278 (1 May 2000); CdSe nanoparticles, described in J. Chem. Phys. 116, 3828-3833 (1 Mar. 2002); $Ho^{3+}$ doped in $BaY_2F_8$, described in Journal of Alloys & Compounds 323, 283-287, and $Ti^{2+}$, $Ni^{2+}$, $Mo^{3+}$, $Re^{4+}$, and $Os^{4+}$ doped chloride and bromide host lattices, for example, $Cs_2ZrCl_6$ doped with $Re^{4+}$ and $Cs_2ZrBr_6$ doped with $Os^{4+}$, described in Journal of Luminescence 83-4, 405-410 (1999), the full disclosures of which are hereby incorporated by reference.

Other examples of up-conversion materials consisting of lanthanoid ions in glasses include erbium doped in a ZnO—$TeO_2$ glass, described in Applied Physics 80, 1752-1754 (2002), and the lanthanide ion pair of $Er^{3+}$ and $Yb^{3+}$ described in Journal of Applied Physics 87, 4274-4278 (2000), the disclosures of which are incorporated by reference. Up-conversion materials are also commercially available, for example, from Phosphor Technology, Ltd. (Essex, England), Lumitek Inc., and Applied Scintillation Technologies.

The phenomenon of up-conversion luminescence, where longer wavelength light is absorbed and shorter wavelength light is emitted, is also explained in the following non-limiting example. For example, in a crystal where $Yb^{3+}$ and $Tb^{3+}$ ions are located close together, cooperative energy transfer can take place. By this energy transfer process, infrared radiation (absorbed by the $Yb^{3+}$ ions) is converted into visible light (emitted as the green $^5D_4$ emissions from the $Tb^{3+}$ ions). In such a process, for example, two excited $Yb^{3+}$ ions simultaneously transfer energy to the $Tb^{3+}$ ion in the ground state, exciting it into a $^5D_4$ level.

A second type of energy transfer is the Auzel-process, or up-conversion. In this process, two step resonant energy transfer occurs and infrared radiation is efficiently converted into visible light. An example of this process is found in $Er^{3+}$ and $Yb^{3+}$ doped glass. In such a case, two $Yb^{3+}$ ions sequentially transfer their energy to the same $Er^{3+}$ ion. The $^2F_{7/2} \rightarrow {}^2F_{5/2}$ transition on the $Yb^{3+}$ ion has a larger optical excitation cross-section than the $^4I_{15/2} \rightarrow {}^4I_{11/2}$ transition of the $Er^{3+}$ ion. As a consequence, with an exciting wavelength of 970 nm, most of the excited ions will be $Yb^{3+}$. The first $Yb^{3+}$ ion brings the $Er^{3+}$ ion into a long-lived intermediate state by energy transfer. The second $Yb^{3+}$ ion excites the $Er^{3+}$ ion further, from which it may decay nonradiatively to the $^4S_{3/2}$ state. Visible luminescence is then seen as a transition from this state to the ground state.

Preferred sensitizers include Yb, which absorbs around 975 nm, and Er which absorbs around 850 nm. Silicon has a band gap near the infrared and generally absorbs in the infrared region around 800 nm up to about 1000 nm.

The sensitizer and acceptor/emitter may be described in terms of energy diagrams. In an energy diagram, each of the horizontal lines represents an energy level. In the case of single atoms such as lanthanoid ions the line is fairly narrow. In the case of semiconductors, the lines become wide bands. In a preferred embodiment, the wavelength of light to be up-converted matches fairly closely an energy line in the sensitizer. At that wavelength, there is maximum absorption. To extend the region of the spectrum that is capable of being up-converted, it will be desirable to provide up-conversion materials not limited to the sharp absorption line of a single lanthanide ion. The range of infrared absorption can be extended by including more than one lanthanide ion in the material as a sensitizer, or by providing non-homogenous environments for the lanthanides in the lattice of the up-conversion material. For example, when lanthanide ions are doped in glasses, the individual ions tend to see slightly different electronic configurations depending on the nearest neighbors in the lattice. The lattice of a glass is inherently disordered. The result is that the absorption line of a lanthanide ion in such a glass is considerably broadened. Up-conversion materials for absorption of a wide range of infrared radiation will generally be composed of a number of different lanthanide ions, lanthanide ions in a glass matrix, or semiconductor materials having a broad band of absorption. Usually, doping of lanthanide ions in glasses is accomplished on the order of 1-10 atom percent.

By using these principles, up-conversion materials having a variety of infrared absorption spectra may be prepared. In one embodiment, up-conversion materials having a narrow infrared absorption spectrum are prepared by, for example, including a single lanthanide ion. In principle, such an up-conversion material will absorb at a single wavelength, and luminesce in the visible. As mentioned above, luminescence in the visible is provided by an acceptor, which may or may not be the same as the lanthanide ion sensitizer. The acceptor absorbs a second photon and luminesces in the visible.

Up-conversion materials with a narrow infrared absorption, and methods for their use, may be useful in a situation where it is desired to illuminate or "paint" an object to be perceived by exposing it, perhaps briefly, to light of a single wavelength. For example, an emitting light of single frequency may be used as a flashlight to tag a target or to illuminate it. The tagging or illumination may be for a brief time, or it may be continuous. Light of a single frequency may be provided by lasers, by light emitting diodes, or by sources of non-classical light. The latter produce light by a process of down-conversion, whereby one photon of a short wavelength produces a pair of photons of longer wavelength, preferably in the infrared. Exemplary materials capable of accomplishing the down conversion are described in Bitton, et al., Phys. Rev. A, 65, 063805 (2002) and Zhang, et al., Phys. Rev. A 64, 033815 (2001), the disclosure of which are incorporated by reference.

Animals with the ability to "see" light of a single wavelength in the infrared region may be readily trained to respond to light of that certain wavelength. An advantage of the method of the invention in this case would be that there would be minimal interference to normal vision, because the light available at any single frequency in the infrared would not be as intense as it would be in the case of broad spectrum vision.

On the other hand, animals having up-conversion materials coupled to their eye that have a broad range of infrared absorption would be able to operate, for example, under conditions of low natural light illumination. In this embodiment, infrared light reflected from objects would be incident on the retina of the animals. The optically coupled up-conversion materials would then efficiently convert the incident infrared radiation of a broad range of wavelengths to light in the visible range that can be perceived by the photoreceptors in the retina of the animal.

In the embodiments discussed above, the invention is practiced whereby an enhanced eye perceives infrared light reflected from an object. Perception of the reflected infrared light proceeds via two-photon antistokes luminescence mediated by nanoparticles that absorb in the infrared and luminescence in the visible. In these embodiments, reflected photons are absorbed by the sensitizers, and reflected photons are also absorbed by the acceptor or emitter to arrive at an excited state that relaxes to the ground state with emission with visible light.

In another preferred embodiment, a source of photons is provided that is separate from the source of reflected photons. In this embodiment, a supplementary photon supply is used to excite the sensitizer of the nanoparticle. Once the nanoparticle is thus sensitized, a single photon from the environment can trigger luminescence of the up-conversion materials in the eye. This leads to a higher yield and greater sensitivity of detection of the reflected photons. In an advantageous embodiment, the method allows vision extension into longer wavelengths, for example from 1 to 11 microns.

In this embodiment, the invention is practiced with at least two sources of infrared light. A first source provides photons that are absorbed by the sensitizer of the nanoparticle and place the nanoparticle into an excited state. The first infrared source may be reflected from an object to be visualized or may be provided separately from the source of reflected light. Preferably, the first infrared source provides photons of a wavelength too short to be doubled by the two-photon absorption and emission such as discussed above. For example, a source of infrared such as a light emitting diode may be provided in goggles or in other apparatus that allows photons to enter through the front of the eye. Alternatively, a source of infrared photons may be applied in the vicinity of the eye, for example by attaching the source to the temples of the subject. In this embodiment, the infrared light from the supplementary photon supply readily penetrates the tissue of the temple and saturates the nanoparticles found inside the eye at the retina and the choroid. Once the source of supplemental photons penetrates the eye, they can be absorbed by the sensitizer of the nanoparticles. In a preferred embodiment, the sensitizers comprise lanthanoid ions.

The method further contemplates the use of a second source of infrared photons for visualization. The second source of infrared photons provides the second photon that leads to luminescence of the up-conversion materials in the visible region. The frequency of emitted light may be calculated algebraically from the frequency of the first infrared source and the frequency of the second infrared source by the simple formula $v_L = v_1 + v_2$, where $v_L$ is the frequency of the luminescence, $v_1$ is the frequency of the first infrared source, and $v_2$ is the frequency of the second infrared source. Equivalently, the wavelength of the luminescence is given by the formula $\lambda_L = \lambda_1 \lambda_2/(\lambda_1 + \lambda_2)$ where $\lambda_L$ is the wavelength of the luminescence, $\lambda_1$ is the wavelength of the first infrared source, and $\lambda_2$ is the wavelength of the second infrared source.

In a preferred embodiment, as noted above, the first infrared source has a wavelength shorter than that which can be doubled by two photon absorption and emission. In a preferred embodiment, $\lambda_1$ is 1,000 nm or less, preferably 900 nm or less, and more preferably 850 nm or less. In one embodiment, $\lambda_1$ is about 690 nm. On the other hand, the second infrared source provides photons having a relatively longer wavelength so that the wavelength of luminescence $\lambda_L$ given in the formula above is in the visible region of the spectrum.

For example, for up-conversion at 1.5 microns (1500 nm, a wavelength used extensively in optical fiber communications), the first source of infrared light may be chosen so that it bathes the eye with 800 nm light. Nanoparticles capable of absorbing infrared light of 800 nm become saturated. In this way, the nanoparticle becomes sensitized, as discussed above. Once sensitized, the particle needs an additional photon with a wavelength of 1.5 microns to release its energy as luminescence at a wavelength equivalent to about 520 nm, calculated from the equation given above. In another non-limiting example, the first infrared source bathes the eye with light of a wavelength of 690 nm. When irradiated with a second infrared source of reflected light having a wavelength of 10.6 nm, the nanoparticle can emit photons having a wavelength of approximately 650 nm, as calculated in the equation above. Advantageously, 10.6 microns (10,600 nm) represents the wavelength of a $CO_2$ laser, commonly used for tagging military targets, for example, in smart bombs.

In a preferred embodiment, a subject, human or non-human, may be provided with a first source of infrared photons. As discussed above, such source may be provided in goggles or in light emitting diodes placed in proximity to the eye, for example at the temples. Advantageously, the first infrared source may be turned on and off so as to provide enhanced perception at the longer wavelengths when needed. In this aspect, the first infrared source would act in a manner similar to earphones that may be turned on or off to enhance perception.

Wavelength shifting materials contain chromophores that can be excited by shorter wavelengths (by one photon excitation) and that luminesce, or emit radiation, at redder wavelengths following excitation. If the chromophore is phosphorescent (emission longer than a microsecond) it can serve to integrate light intensity and help in low lighting conditions. For the case of wavelength shifting materials having chromophores with very long phosphorescence time, an animal subject with such materials optically coupled to the eye would be able to visualize the paths of moving objects, which may be advantageous in certain cases. Further, if a person has lost the blue (or green) detecting photoreceptors, the person would be able to see those wavelengths after they are shifted to longer wavelengths by wavelength shifting materials in the eye. This technique could be used in animals that are not capable of seeing in the 400-450 nm portion of the spectrum.

Non-limiting examples of wavelength shifting materials include CdSe nanoparticles, rhodamine dyes, and fluorescent dyes. Such materials are commercially available, for example from Exciton or Lambda Physik.

For long-lived phosphorescence zinc sulfide is a preferred material. The peak spectral distribution of the emitted light roughly coincides with the peak spectral sensitivity of the human visual system under scotopic (low-level) lighting conditions (which is around 510 nanometers). Zinc sulfide occurs in crystalline form, but it is not photoluminescent by itself. Generally, to provide photoluminescence, activator ions may be added to the crystals. A non-limiting example of a suitable activator ion is copper. The activator ions in the zinc sulfide absorb the excitation energy of the ultraviolet or visible light and later release it as visible light. Phosphorescent materials are commercially available, for example from Imperial Materials Ltd—Photoluminescent Products, Luna Technologies International, Inc., and Lumilux.

Conveniently, the up-conversion materials and wavelength shifting materials may be supplied in the form of nanoparticles. As used in this application, nanoparticles refer to particles having a diameter between about 3 nm and about 100 nm, more preferably between about 5 nm and about 50 nm.

In one embodiment, the nanoparticles contain polymeric nanospheres, for example as described in Thomas, et al., Fresenius J. Anal. Chem. 369, 477-482 (2001), the entire disclosure of which is incorporated by reference. To produce the polymeric nanospheres, methacrylate may be used as monomer to reduce random absorption of proteins onto the nanosphere surfaces. The acid group surface functionalization of such polymeric nanospheres allows the nanospheres to be conjugated to reactive groups such as amine groups on antibodies, as discussed further below. Polymeric nanospheres can be made biodegradable to limit the duration of vision enhancement and to provide a safe elimination pathway.

In another embodiment, nanoparticles having diameters in the desired range may be synthesized having a silica shell according to known methods, such as for example those disclosed in Santra, et al., Analytical Chemistry 73, 4988-4993 (2001), and Patra, et al., J. Phys. Chem. B 106, 1909-1912 (2002), the full disclosures of which are herein incorporated by reference. In this embodiment, nanoparticles are prepared using a water and oil microemulsion method. The controlled hydrolysis of a tetraalkyl orthosilicate in the microemulsion leads to formation of monodisperse luminophore-doped silica nanoparticles. The luminophores, such as lanthanoid ions, are doped inside the nanoparticles.

Nanoparticles with well-defined sizes may be prepared by the oil and water microemulsion method. In the well-known method, a surfactant is dissolved in a hydrocarbon, such as isooctane or cyclohexane. An aqueous solution of a lanthanoid ion may then be added to the solution of surfactant in hydrocarbon to form a microemulsion. To this microemulsion, a silicon precursor is added, for example in the form of a tetraalkoxysilane such as tetraethoxysilane (TEOS). After the mixture is stirred for a period of minutes to a period of a few hours, $SiO_2$ particles doped with the lanthanide ions are obtained. The dispersed $SiO_2$ particles doped with lanthanide ions may be harvested by centrifuging and rinsing with a solvent such as acetone. Altering the water to surfactant ratio regulates the size of the particles being synthesized. The size of $SiO_2$ particles prepared by the microemulsion method may be measured by dynamic light scattering or transmission electron microscopy.

In a preferred embodiment, titanum may be added as, for example, titanum n-butoxide at the level of about 5%. It has been found that such results in higher up-conversion efficiency. Thus, Er doped $SiO_2$ and $SiO_2$—$TiO_2$ sol gel silicate glasses may be prepared, such as disclosed in Boye, et al., Journal of Luminescence 94, 279-282 (2001), the disclosure of which is herein incorporated by reference. Similar methods may be used to synthesize Er, Yb co-doped $Y_2O_3$ and Tm—Yb co-doped $Y_2O_3$. The microemulsion method described above can be used to synthesize nanoparticles containing lanthanoid ions by dissolving salts such as $ErCl_3$ in an aqueous solution, prior to the addition of the silicon precursor.

In one embodiment, nanoparticles containing up-conversion materials or wavelength shifting materials such as described above may be delivered directly to the eye, by procedures described further below. In another embodiment, the nanoparticles may be covalently coupled to antibody molecules.

To couple the nanoparticles to antibody molecules, the nanoparticle may first be reacted with a coupling molecule. The coupling molecule contains a functional group that will react with reactive groups on the surface of the nanoparticles, and further contains chemical groups that will react with functional groups on the antibody molecules. The respective reactive groups on the coupling molecule are preferably separated by a spacer group having a length of 3 carbon bonds or more. In a preferred embodiment, the spacer group is provided by a (—$CH_2$)$_3$— group.

The functional group on the coupling molecule reactive with the surface groups on the nanoparticles may be conveniently selected from trialkoxylsilanyl compounds in the case of nanoparticles made of $SiO_2$. The chemical group reactive with functional groups on the antibody may be selected from a wide variety of groups. Among these are amino, urea, and carboxylic acid. They react with functional groups on the antibodies such as, without limitation, terminal amino and carboxyl groups, carboxyl groups on amino acid side chains such as aspartic acid and glutamic acid, amino groups on lysine side chains, and the like. Suitable coupling molecules include, without limitation, 3-(triethoxylsilanylpropyl-carbamoyl)-butyric acid, 3-aminopropyltrimethoxysilane, and trimethoxysilyl propyl urea. When a nanoparticle containing $SiO_2$ groups on the surface is dissolved in a solution containing these or other coupling molecules, the silica will bind to the silyl groups, forming a derivatized nanoparticle.

Specific proteins may be coupled to the derivatized nanoparticles, taking advantage of the reactivity of the functional groups on the derivatized nanoparticles with functional groups on the proteins, as discussed above. It is preferred to couple the derivatized nanoparticles to antibodies specific for antigens on biomaterials of the eye, for example on protein components of the eye. Such protein components of the eye include without limitation, rod proteins, cone proteins, ROM-1, peripherin, X-arrestin, S-antigen, and rhodopsin. ROM-1 and peripherin are preferred targets, because they are found in the structural walls of the outer segments of rods and cones. These protein components of the eye are found in the vicinity of the retina and epithelium. The antibodies provide for a specific binding to antigens on the protein components. The protein components are located in proximity to the photoreceptors of the eye. Accordingly, upon binding, the antibody coupled nanoparticles deliver up-conversion or wavelength shifting materials optically coupled to the photoreceptors. Significantly, the materials are coupled to the photoreceptors behind the lens, so that incident light is focused upon the retina by the native optics in the eye and images on the up-conversion materials.

Preparation of antibodies is well known in the art. In a typical procedure, an antibody is prepared taking advantage of an animal's response to the presence of a foreign substance. An antigen is injected into an animal, and after a certain time, antibodies of a class termed IgG (immunoglobulin G) that react specifically with the introduced protein antigen can be harvested from the animal's serum. Each antibody has a specific affinity for a particular region of the antigen protein. This region is termed an epitope. Thus, antibodies may be raised to epitopes on the antigenic protein. These antibodies are then bound to the derivatized nanoparticles to prepare a targeted up-conversion nanoparticle conjugate.

Antibodies may be produced by standard biochemical methods. Because many antibodies are cross-reactive, it is possible to prepare antibodies for use in, say, humans, by raising antibodies to an antigen injected in other host species, such as mice, rats, or sheep. Likewise, many host animals produce antibodies that are reactive in dogs. In many cases, antibodies to protein components of the eye are commercially available. For example, mouse and rabbit anti-peripherin polyclonal and monoclonal antibodies reactive in humans are commercially available from CHEMICON, Novus Biological, and United States Biological. Similarly, mouse anti-arrestin monoclonal antibodies reactive in humans are commercially available from BD Biosciences Pharmingen. Likewise, mouse anti-rhodopsin monoclonal antibodies reactive in humans are commercially available from CHEMICON and Lab Vision. These and other antibodies may be readily located by contacts with suppliers such as mentioned above. Sources of antibodies to eye protein components reactive in humans are also readily searchable on web sites such as, for example, www.biocompare.com.

Conjugation of the derivatized nanoparticle to the antibody is generally performed by stirring together a solution of the nanoparticle and antibody. Coupling of the derivatized nanoparticle to the antibody to form a conjugate proceeds under relatively mild conditions. In a preferred embodiment, stoichiometric ratios of derivatized nanoparticle and antibody molecules are chosen so that on average from 1 to 20 antibody molecules are attached to each derivatized nanoparticle. In one embodiment, from 2 to 10 and more preferably about 5 antibody molecules are attached per nanoparticle. In another preferred embodiment, one or two antibody molecules are attached per nanoparticle.

Delivery of the up-conversion materials into the eye to optically couple them to the photoreceptors may be accomplished with a number of procedures. Although delivery by eye drops is possible, it is in general less preferred. It is known that many drugs can be transferred through the cornea only with difficulty to reach the retina, because of the blood-aqueous barrier and because the internal flux of the eye is opposed to penetration of external fluids. The up-conversion materials may be delivered by the systemic route, such as by injecting them into the blood stream. A drawback of this method is that it may take longer to achieve optimum concentration of the materials in the eye. Another alternative for delivering the up-conversion materials to the eye is by direct injection. Although such a method is effective, it is less preferred because of pain, possible inflammation and fear induced in the individual on which it is practiced.

In a preferred embodiment, the up-conversion materials of the invention are delivered to the photoreceptors of the eye using iontophoresis. Iontophoresis is based on the principle of using an electric field, created by a low voltage current, to change the permeability of cells and to ionize drug materials thereby allowing the materials to be delivered through different tissues to a targeted area. Iontophoresis is useful to treat parts of the body where drugs and other materials cannot be readily introduced by other means such as local injection, regional and general injection, or oral administration.

In a preferred embodiment, an iontophoresis apparatus for ocular delivery is used that comprises a housing element formed to cooperate with the eye. Such a device is described for example in Beck, U.S. Pat. No. 6,319,240, the full disclosure of which is incorporated by reference. The ocular iontophoresis device has two parts: a disposable ocular applicator that receives the drug, and a battery powered micro-generator with automatic control features connected to a return electrode, advantageously connected to a patch for attachment to the forehead. The applicator, including tubes, syringes and micro-generator lead is sterile, sealed into a blister pack, the whole being disposable. In a preferred embodiment, the iontophoresis device delivers constant amounts of drugs or other materials to the posterior chamber of eye, particularly the choroid and the retina.

In a preferred embodiment, a solution containing the up-conversion materials, preferably either in the form of nanoparticles or of nanoparticles conjugated to an antibody molecule is delivered by syringe into the ocular applicator. The up-conversion materials are then delivered by the ocular iontophoresis device into the posterior segment of the eye, and especially into the subretinal space to reach the retina and the choroid. In one embodiment, a first dose may be administered and the response of the subject to infrared light tested. If the response is not adequate for the contemplated use, a subsequent dose or doses of up-conversion materials may be added as a supplement. Advantageously, hospitalization is not required for administering the up-conversion materials by the iontophoresis method.

The amount of up-conversion materials to be delivered to the eye will in general vary according to the individual, the conditions under which the invention is to be practiced, and other factors. One method to estimate the amount of material needed is illustrated by the following example. Assuming there are approximately $10^8$ photoreceptors in the retina, a fully loaded photoreceptor could have as many as 100 nanoparticles, and assuming 1% efficiency in targeted delivery, it can be estimated that about $10^{12}$ particles would be required for a dose. If the nanoparticles have a density of $2.2 \text{ g/cm}^3$ and an average size (diameter) of 10 nm, it can be shown that $10^{12}$ particles represents a dose of about 3 micrograms ($3 \times 10^{-6}$ g). Similar calculations may be made taking into account the configuration of the animal's eye, and the density and size of the nanoparticles.

The up-conversion materials or wavelength shifting materials may be applied by any of the above methods to one or both eyes of the animal. If the materials are delivered to only one eye, then generally the animal is left with one unaffected eye. Such may be desirable because it is simpler to administer, it leaves the animal with a working eye in case of allergic reaction or other complication, and it allows the animal to operate normally without enhancement by wearing an eye patch. On the other hand, for true binocular vision, or to provide other advantages, it is preferred to provide both eyes with the enhanced vision.

The up-conversion materials, and the up-conversion material antibody conjugates may be tested in vitro for specificity. When used in vivo, such as when they are delivered to the retina, the up-conversion materials can be imaged in the eye using low intensity infrared light, for example from a light emitting diode. Such light emitting diodes may be incorporated into any type of device used to image the retina, for example an ophthalmoscope. If the subject into which the up-conversion materials are optically coupled is a human, the subject will be able to tell the administrator whether vision is available. In other animals, the response of the retina cells may be measured directly.

EXAMPLE

Sodium bis(2-ethylhexyl) sulfosuccinate (AOT, Sigma) is dissolved in cyclohexane at 0.3 M. An aqueous solution is prepared of $ErCl_3$ at 0.1 M. The oil-based and the water-based solutions are mixed in equal parts to form a microemulsion. To this microemulsion, tetraethoxysilane (Aldrich, TEOS, 99.99%) is added as the Si precursor. The mixture is stirred for 12 hr at room temperature. Dispersed $SiO_2$ nanoparticles in cyclohexane are then centrifuged at 15,000 rpm and the particles are rinsed repeatedly with acetone. The size of the nanoparticles is confirmed by transmission electron microscopy. The up-conversion efficiency is tested with a light emitting diode with output near 850 nm. The size of the nanoparticles can be adjusted by varying the amount of aqueous vs. oil volumes. The up-conversion efficiency is adjusted by the concentration of lanthanum salt and the addition of other sensitizer and acceptor ions (in the form of water soluble salts).

The up-conversion nanoparticles may be dissolved in an isotonic solution compatible with the iontophoresis device at a concentration of 0.1 mg/ml. The amount of up-conversion material required per eye is in the range of 0.05 to 0.5 micrograms.

The up-conversion nanoparticles can be functionalized by reaction with trimethoxysilylpropyl urea. An aqueous solution of trimethoxysilylpropyl urea at 10 mM concentration is prepared. To this solution 2 g of the particles are added (equivalent to 1 mM). This adds approximately 10 functional groups in each nanoparticle.

The functionalized particles (10 microliter of the previous solution) are then reacted with 10 microliter anti-peripherin monoclonal antibody as supplied by Novus Biologicals. The mixture is incubated for 24 hrs at 4° C. These particles can be tested in vitro using retinal tissue from animals and a microscope illuminated with infrared light from a light emitting diode. If the specificity and efficiency are satisfactory the particles are ready for delivery.

The animal or human to be given enhanced vision receives a topical anesthetic (such as Proparacaine) in the form of eye drops. The disposable ocular applicator for iontophoresis is adjusted in one of the eyes. The solution containing the up-conversion materials, either in the form of nanoparticles or of nanoparticles conjugated to an antibody molecule is delivered by syringe into the ocular applicator. One microliter of the above solution per eye is sufficient, and this is added to the iontophoresis electrolytic solution. The battery powered micro-generator with automatic control features connected to a return electrode, is connected to a patch for attachment to the forehead and activated. The up-conversion materials are delivered by the ocular iontophoresis device into the posterior segment of the eye, and especially into the subretinal space to reach the retina and the choroid. If the subject is having both eyes treated, the second eye is treated in a similar fashion.

Vision acuity in the infrared can then be tested one or more hours after iontophoresis. For this test it is important to use a vision chart illuminated by infrared light in the desired wavelength region. An ophthalmoscope with an LED emitting infrared light can be used to determine the location of the up-conversion nanoparticles; the nanoparticles may be observed in the retina as a faint green or orange glow depending on the emitter.

The description of the invention is merely exemplary in nature and, thus, variations that do not depart from the gist of the invention are intended to be within the scope of the invention. Such variations are not to be regarded as a departure from the spirit and scope of the invention.

I claim:

1. A method for enhancing vision in an animal under conditions of low intensity light comprising delivering up-conversion materials to the eye of the animal,
   wherein the up-conversion materials absorb infrared light, and
   wherein the up-conversation materials luminescence in the visible range of the electromagnetic spectrum.

2. A method according to claim 1, further comprising exposing the eye of the animal to a source of light of a wavelength sufficient to excite the up-conversion materials.

3. A method according to claim 1, wherein the up-conversion materials comprise one or more lanthanoid ions.

4. A method according to claim 1, wherein the up-conversion materials comprise a semiconductor with a band gap in the infrared.

5. A method according to claim 3, wherein the lanthanoid ion is selected from the group consisting of Pr, Nd, Eu, Er, Gd, and Yb.

6. A method according to claim 5, wherein the lanthanoid ion comprises Er.

7. A method according to claim 1, wherein the up-conversion materials are in the form of nanoparticles.

8. A method according to claim 7, wherein the nanoparticles comprise $SiO_2$.

9. A method according to claim 7, wherein the nanoparticles comprise CdSe.

10. A method according to claim 1, wherein the up-conversion materials comprise a lanthanoid ion in a glass.

11. A method according to claim 7, wherein the nanoparticles are covalently bound to an antibody, wherein the antibody is specific for an antigen on a protein component of the eye.

12. A method according to claim 11, wherein the antibody is an antibody specific for a rod protein.

13. A method according to claim 11, wherein the antibody is specific for a cone protein.

14. A method according to claim 11, wherein the antibody is specific for ROM-1.

15. A method according to claim 11, wherein the antibody is specific for peripherin.

16. A method according to claim 11, wherein the antibody is specific for arrestin.

17. A method according to claim 11, wherein the antibody is specific for rhodopsin.

18. A method according to claim 1, wherein delivering the up-conversion material to the eye is carried out with iontophoresis.

19. A method according to claim 1, wherein the animal is a human.

20. A method according to claim 1, wherein the animal is non-human.

21. A composition comprising a nanoparticle covalently bound to an antibody, wherein the nanoparticle comprises an up-conversion material that absorbs electromagnetic radiation having a wavelength greater than about 650 nm and luminesces in the visible region of the electromagnetic spectrum, and the antibody is an antibody specific to a protein component of the eye.

22. A composition according to claim 21, wherein the antibody is specific to an antigen selected from the group consisting of rod proteins, cone proteins, ROM-1, peripherin, arrestin, S-antigen, and rhodopsin.

23. A composition according to claim 21, wherein the up-conversion material comprises one or more lanthanoid ions.

24. A composition according to claim 21, wherein the up-conversion material comprises a semiconductor having a band gap in the infrared.

25. A composition according to claim 21, wherein the nanoparticles comprise $SiO_2$.

26. A composition according to claim 21, wherein the nanoparticles comprise an organic polymer.

27. A composition according to claim 21, wherein the antibody is an antibody specific to peripherin.

28. A composition according to claim 21, wherein the antibody is an antibody specific to ROM-1.

29. A method of providing a living being with enhanced vision, the method comprising placing nanoparticles adjacent a retina of at least one eye of the living being, wherein the nanoparticles are bound to an antibody that preferentially binds to a portion of one of the biomaterials in the eye.

30. The method according to claim 29, wherein the nanoparticles absorb infrared and luminesce visible light.

31. A method of providing a living being with enhanced vision, the method comprising placing nanoparticles adjacent a retina of at least one eye of the living being, wherein the nanoparticles comprise one or more lanthanoid ions.

32. The method according to claim 31, wherein the nanoparticles comprise two or more different lanthanoid ions.

33. A method of providing a living being with enhanced vision, the method comprising placing nanoparticles adjacent a retina of at least one eye of the living being, wherein the nanoparticles comprise a semiconductor material having a band gap in the infrared.

34. The method according to claim 31, wherein the nanoparticles are bound to an antibody that preferentially binds to a portion of one of the biomaterials in the eye.

35. The method according to claim 29, wherein the antibody is an antibody to a rod protein.

36. The method according to claim 29, wherein the antibody is an antibody to a cone protein.

37. The method according to claim 29, wherein the antibody is an antibody to ROM-1.

38. The method according to claim 29, wherein the antibody is an antibody to peripherin.

39. The method according to claim 29, wherein the antibody is an antibody to X-arrestin.

40. The method according to claim 29, wherein the antibody is an antibody to S-antigen.

41. The method according to claim 29, wherein the antibody is an antibody to rhodopsin.

42. The method according to claim 29, wherein the nanoparticles are optically coupled to photoreceptor cells of the living being which is a human.

43. The method according to claim 29 wherein the living being is a dog.

44. A method for visualizing an object under conditions of low ambient light comprising:
  exposing the object to incident electromagnetic radiation having a wavelength greater than what can be seen by the naked eye; and
  perceiving light reflected from the object with an enhanced eye,
  wherein the enhanced eye comprises an up-conversion material optically coupled to the photoreceptors of the eye,
  wherein the up-conversion material absorbs light of the wavelength reflected from the object, and luminesces in the visible region of the electromagnetic spectrum.

45. A method according to claim 44, wherein the up-conversion material comprises one or more lanthanoid ions.

46. A method according to claim 44, wherein the up-conversion material comprises two or more different lanthanoid ions.

47. A method according to claim 44, wherein the up-conversion material comprises a semiconductor having a band gap in the infrared.

48. A method according to claim 44, wherein the up-conversion material is in the form of a nanoparticle covalently bound to an antibody, wherein the antibody is specific for an antigen in a biomaterial found in the eye.

49. A method according to claim 48, wherein the antibody is an antibody to a rod protein.

50. A method according to claim 48, wherein the antibody is an antibody to a cone protein.

51. A method according to claim 48, wherein the antibody is an antibody to ROM-1.

52. A method according to claim 48, wherein the antibody is an antibody to peripherin.

53. A method according to claim 48, wherein the antibody is an antibody to S-antigen.

54. A method according to claim 48, wherein the antibody is an antibody to X-arrestin.

55. A method according to claim 44, wherein the incident electromagnetic radiation is light of a single frequency.

56. A method according to claim 44, wherein the incident electromagnetic radiation is coherent laser light.

57. A method according to claim 55, wherein the source of the light is a light emitting diode.

58. A method according to claim 44, wherein the object is continuously illuminated.

59. A method according to claim 44, wherein the object is illuminated by a source of non-classical light.

60. A method according to claim 44, further comprising providing a source of photons separate from the light reflected from the object, wherein the photons excite the up-conversion materials.

61. A method for visualizing an object with an enhanced eye, wherein the enhanced eye comprises an up-conversion material optically coupled to the photoreceptors of the eye, comprising
  providing the eye with a first source of photons that sensitize the up-conversion material; and
  providing the eye with a second source of photons reflected from the object, wherein the up-conversion material absorbs the light reflected from the object.

62. A method according to claim 61, wherein the first source of photons is delivered to the eye without reflecting off the object.

63. A method according to claim 61, wherein the first source of photons has a wavelength of 1000 nm or less.

64. A method according to claim 61, wherein the second source of photons has a wavelength of 1500 nm or greater.

65. A method according to claim 61, wherein the second source of photons is from a $CO_2$ laser.

66. A method according to claim 61, wherein the first source of photons is provided by a light emitting diode.

67. A method according to claim 61, wherein the up-conversion material is in the form of nanoparticles.

68. A method according to claim 67, wherein the nanoparticle is covalently bound to an antibody for a protein component of the eye.

69. A method according to claim 67, wherein the antibody is an antibody specific for ROM-1 or peripherin.

70. A method of providing a living being with enhanced vision, the method comprising placing nanoparticles adjacent a retina of at least one eye of the living being, wherein the nanoparticles vary light focused through a lens of the eye.

71. A method of providing a living being with enhanced vision, the method comprising placing nanoparticles adjacent a retina of at least one eye of the living being, further comprising using the nanoparticles to shift light wavelengths in the eye.

72. The method according to claim 29, wherein the nanoparticles each have a diameter between 5 nm and 50 nm.

73. The method according to claim 29, wherein the nanoparticles are polymeric nanospheres.

74. The method according to claim 29, further comprising preparing the nanoparticles using water and oil microemulsion.

75. The method according to claim 29, further comprising delivering the nanoparticles to the retina by iontophoresis.

76. The method according to claim 70, wherein the nanoparticles each have a diameter between 5 nm and 50 nm.

77. The method according to claim 70, wherein the nanoparticles are polymeric nanospheres.

78. The method according to claim 70, further comprising preparing the nanoparticles using water and oil microemulsion.

79. The method according to claim 70, further comprising delivering the nanoparticles to the retina by iontophoresis.

80. The method according to claim 70, wherein the nanoparticles are optically coupled to photoreceptor cells of the living being which is a human.

81. The method according to claim 71, wherein the nanoparticles each have a diameter between 5 nm and 50 nm.

82. The method according to claim 71, wherein the nanoparticles are polymeric nanospheres.

83. The method according to claim 71, further comprising preparing the nanoparticles using water and oil microemulsion.

84. The method according to claim 71, further comprising delivering the nanoparticles to the retina by iontophoresis.

85. The method according to claim 71, wherein the nanoparticles are optically coupled to photoreceptor cells of the living being which is a human.

* * * * *

UNITED STATES PATENT AND TRADEMARK OFFICE
CERTIFICATE OF CORRECTION

PATENT NO.        : 8,185,209 B2
APPLICATION NO.   : 10/749095
DATED             : May 22, 2012
INVENTOR(S)       : Marcos Dantus Page 1 of 1

It is certified that error appears in the above-identified patent and that said Letters Patent is hereby corrected as shown below:

Title page
Item [56] References Cited, OTHER PUBLICATIONS,
Page 1, line 13 "Joouornal of Pharmaceutics" should be --Journal of Pharmaceutics--.
Page 2, line 26 (left column) "J.F. Suyer" should be --J.F. Suyver--.
Page 2, line 47 (left column) "($^4F_{frax:9;2}$ $^4I_{frax:15;2}$)" should be --"($^4F_{9;2}$ $^4I_{15;2}$)--.
Page 2, line 50 (right column) "Fas-medisted" should be --Fas-mediated--.

Signed and Sealed this
Nineteenth Day of August, 2014

Michelle K. Lee
*Deputy Director of the United States Patent and Trademark Office*